United States Patent [19]

Kohler

[11] Patent Number: 4,776,297
[45] Date of Patent: Oct. 11, 1988

[54] APPARATUS FOR COATING THIN LAYER CHROMATOGRAPHIC PLATES

[75] Inventor: Dale L. Kohler, Ponca City, Okla.

[73] Assignee: Conoco Inc., Ponca City, Okla.

[21] Appl. No.: 83,540

[22] Filed: Aug. 7, 1987

[51] Int. Cl.⁴ .............................................. B05C 5/02
[52] U.S. Cl. .................................. 118/663; 118/413; 118/415
[58] Field of Search .................. 118/415, 413, 663

[56] References Cited

U.S. PATENT DOCUMENTS 3,145,410  8/1964  Stahl ................................ 118/415 X
3,970,040  7/1976  Porth ............................... 118/415 X Primary Examiner—John McIntosh
Attorney, Agent, or Firm—Richard K. Thomson

[57] ABSTRACT

Apparatus for uniformly coating thin layer chromatographic plates. A plate holder secures a plurality of chromatographic plates while a metering device with an adjustable doctor blade is drawn over their surface at a uniform speed by a variable speed motor.

5 Claims, 1 Drawing Sheet

APPARATUS FOR COATING THIN LAYER CHROMATOGRAPHIC PLATES

BACKGROUND AND SUMMARY OF THE INVENTION

In thin layer chromatography, sample plates are coated with a suitable "stationary phase" material such as a silica gel, for example. It is essential that this gel coating layer be uniform and continuous over the entire surface of the plate. The coated plates are subsequently placed in racks and the coating is allowed to dry. Once dried, the coated surface of the plate may be etched to form a plurality of narrow columns upon which sample analysis using chromatographic separation can be performed. A measured amount of a sample in its carrier, collectively identified as the "mobile phase", which may be a gas, liquid, or solid in solution, is introduced to the entry end of a column. The sample is then eluted using one or more solvents causing chemical separation along the column.

Some difficulty has been encountered in obtaining chromatographic plates of suitable quality. Manual application techniques typically result in 20 to 40% of the plates being discarded due to non-uniform coating. Such a non-uniform coating could effect the propagation rate of the sample along the column thereby affecting the outcome of the sample analysis. Until recently, satisfactory plates were available from a particular supplier. However, recent retirement of one or more of the supplier's key employees has resulted in degradation of the quality of plates available, thereby resulting in the experimentation that led to the present invention.

The present invention seeks to overcome the problems leading to the above-mentioned control difficulties. A plate holder for a glass sheet of sufficient length to form a plurality of chromatographic plates has lateral and longitudinal edge guides for positioning the plate. The plate holder further has a substantially smooth vertical surface along its upper edge. A guide bar on a liquid metering device engages the smooth vertical surface to guide the metering device and properly locate if relative to said chromatographic plates as it travels over the plates dispensing its coating. An adjustable doctor blade smooths out the coating uniformly over the surface of the plates. A motor draws the metering device along at a constant speed by means of a cable or cord to insure uniformity of the coating thickness. The motor preferably has a reostatic control associated with it so that the speed of movement of the metering device can be varied to suit the viscosity characteristics of the coating material being applied.

Various other features, advantages and characteristics of the apparatus of the present invention will become apparent after a reading of the following detailed description.

DETAILED DESCRIPTION

Figure 1:
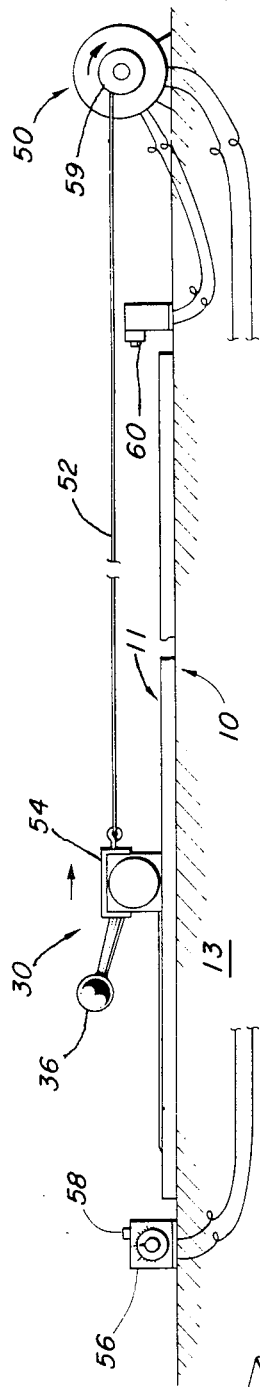
FIG. 1 is a side view of the coating apparatus of the present invention.
Figure 2:
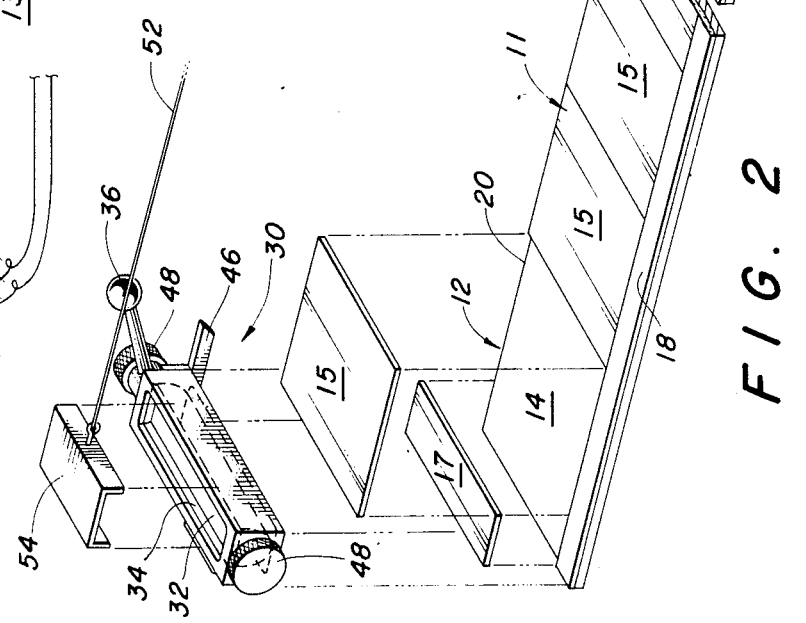
FIG. 2 is an exploded isometric view of a portion of the apparatus shown in FIG. 1.

The coating apparatus of the present invention, as best seen in FIGS. 1 and 2, has three primary components: plate holder 10, metering device 30, and motor means 50.

Plate holder 10 comprises a panel 12 whose upper surface defines a flat planar surface 14. A lateral guide 16 is affixed to one edge of surface 14 projecting above that surface a distance equal to the thickness of a sheet of glass 11 supported upon holder 10. A longitudinal guide 18 is affixed to the planar surface 14 along the lower edge of panel 12 and also projects above the surface a distance equal the thickness of glass sheet 11. The surface area of planar surface 14 bounded by lateral guide 16 and longitudinal guide 18 is substantially equal to the surface area of glass sheets 11. The upper edge 20 of holder 10 defines a smooth vertically extending surface.

Figure 3:
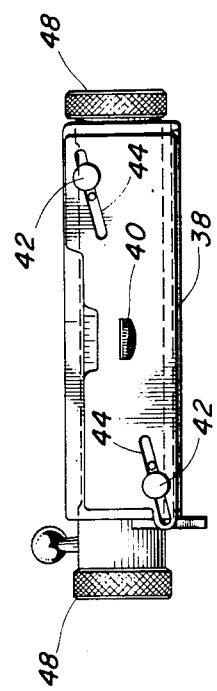
FIG. 3 is a detailed side view of the back side of the metering device that forms a part of the present invention.

Metering device 30 is an off-the-shelf item that includes a reservoir 32 that has an opening 34 therein. When the handle 36 is in the position shown in FIG. 2, opening 34 is upward and liquid is maintained in reservoir 32 which is shaped in the form of a partial cylinder. When the handle 36 moves to the position shown in FIG. 1, opening 34 is shifted to the bottom of metering device 30 and the liquid in reservoir 32 is permitted to flow out of reservoir 32. A doctor blade 38 (FIG. 3) insures the liquid coating material is spread evenly over the surface of glass plate 11. Position of the blade 38 can be varied to change the thickness of the coating applied to glass sheet 11 as shown by adjustment 40 by loosening screws 42 and repositioning the doctor blade 38 by shifting it using slots 44 to adjust the distance between doctor blade 38 and the surface of glass plate 11. Screws 42 are then retightened in slots 44 to maintain the adjusted position of blade 38. Guide bar 46 extends below and laterally to one side of reservoir 32. End discs 48 are connected to and rotate with the partially cylindrical reservoir 32.

Motor means 50 is connected to the metering device 30 by a cable or cord 52 and a channel member 54 that can be removably slipped over the top of device 30 without affecting the operation of reservoir 32 and can easily be removed to permit the reservoir to be refilled. Motor means 50 may be a variable speed motor or, as shown in FIG. 1, may be equipped with a separate reostat 56 to permit the speed of movement of the metering device over glass sheet 11 to be adjusted to best suit the viscosity and flow characteristics of the particular coating material being used. a switch 58 shown here on the reostat 56, permits the remotely located motor means 50 to be started from a point adjacent the lead end of plate holder 10. Motor means 50 will wind cord 52 onto spool 59 and draw metering device 30 to the right in FIG. 1. A limit switch 60 positioned adjacent the tail end of holder 10 is contacted by the metering device 30 to shut off motor 50. It will of course be understood that switch 60 could be located elsewhere and contacted by a pin, or the like, attached to cable 52. Further, other types of motor means 50 could be used such as a conventional helical drive, or the like.

In use, plate holder 10 may be clamped or bolted to a table or work bench 13. If holder 10 is bolted, the bolt or screw heads will be countersunk so that no fastener protrudes above planar surface 14 lateral guide 16, or longitudinal guide 18. Glass plate 11 is placed in holder 10 in contact with lateral guide 16 and longitudinal guide 18 and the surface etched with a glass cutter to define individual chromatographic plates 15 which, by way of example and not limitation, are 7⅜" square. In laying out the glass sheet 11, an entry end piece 17 of 2⅜" and a tail piece 19 of 2" will be left on opposite sides of the chromatographic plates 15. Again, by way of example, glass sheet 11 is 44" thereby making five chromatographic plates 15.

A liquid coating mixture, which may be silicon gel made of 50 ml of dry silicon powder and 100 ml of water, is prepared and poured into reservoir 32. Metering device 30 is placed above the entry end piece 17 of glass sheet 11. Metering device 30 sits atop sheet 11 and longitudinal guide 18. Guide bar 46 engages smooth vertically extending surface 20 to properly position metering device 30 with respect to chromatographic plates 15. If desired, a second vertically extending surface (not shown) could be clamped adjacent the first and spaced therefrom by a distance equal to the width of guide bar 46 to prevent the meterig device from wandering. Otherwise, manual pressure will normally be necessary as metering device 30 is in motion.

Handle 36 is moved to the FIG. 1 position and switch 58 is energized to start motor means 50. (It will be understood that the position of doctor blade 38 and speed for reostat 56 will have been preset for the particular coating thickness desired and the viscosity characteristics of the coating material, respectively.) The entry end piece 17 allows the coating material to be flowing properly from reservoir 32 before coating of plates 15 begins. Similarly, tail end piece 19 enables the metering device 30 to clear the last plate before metering device 30 contacts limit switch 60 turning off motor 50. As the coating run is completed, handle 36 is manually returned to the FIG. 2 position closing reservoir 32. This could obviously be done mechanically by contacting a friction plate, or the like, with either end disc 48. Chromatographic plates 15 are lifted off surface 14 and placed in a drying rack (not shown). End pieces 17 and 19 are discarded and metering device 30 is manually returned to the leading end of holder 10. A second cable or cord (not shown) could be attached to metering device 30 to permit a reversible motor 50 to return it to starting position after the coated chromatographic plates have been removed.

The coating apparatus of the present invention, by enabling a metering device to be drawn over the surface to be coated with a uniform speed, provides a simple, yet effective means to provide a chromatographic plate with the thin, uniform coating needed for proper performance.

Various changes, alternatives, and modifications will become apparent to a person of ordinary skill in the art after reading the foregoing description. It is intended that all such changes, alternatives and modifications as come within the limitations of the appended claims be considered part of the present invention.

I claim:

1. Apparatus for uniformly coating chromatographic plates with a thin layer of absorptive material which supports and retains a plurality of samples, said apparatus comprising:

a plate holder for securing in place a plurality of chromatographic plates which have a collective first length, a uniform width and thickness, said plate holder including a substantially flat first planar surface having a second length which is at least equal to said collective first length of said plates, a lateral positioning guide extending along one lateral edge of said first planar surface and protruding thereabove a distance substantially equal to the thickness of said plates for providing a lateral reference surface for said chromatographic plates, a longitudinal positioning guide extending along one longitudinal edge of said first planar surface and also extends above said planar surface a distance substantially equal to the thickness of said plates for providing a longitudinal reference surface for said chromatographic plates, a smooth vertically extending surface formed on the second longitudinal edge of said plate holder;

a metering device for regulating the flow of a liquid coating onto an upper surface of said plurality of chromatographic plates as it slides thereover, said metering device including a reservoir of material, a movable outlet for distributing material from said reservoir, an adjustable doctor blade for varying the thickness of said coating and a guide bar extending downwardly from one end of said reservoir, said guide bar engaging said smooth vertically extending surface to properly locate said metering device with respect to said chromatographic plates;

a tow cord, means for removably securing said tow cord to said metering device;

an electric motor means connected to said tow cord for drawing said metering device over the upper surface of said chromatographic plates at a uniform speed so as to provide said plates with a continuous coating of uniform thickness.

2. The coating apparatus of claim 1 further comprising means to vary the speed of said electric motor means to provide a suitable uniform rate of travel appropriate for the proper spreading of said coating material.

3. The coating apparatus of claim 1 wherein said electric motor means is remotely located from said plate holder and said apparatus further comprises switch means proximate said plate holder for actuating said electric motor means.

4. The coating apparatus of claim 3 further comprising a limit switch located adjacent the end of said plate holder in a position where it may be contacted by said metering device or some means operatively associated therewith, to shut off said electric motor means after said metering device has completed its course of travel.

5. The coating apparatus of claim 1 wherein said means for removably securing said tow cord to said metering device comprises a channel member which slides downwardly over an upper portion of said metering device and which may be easily removed to facilitate refilling said reservoir.

* * * * *